(12) United States Patent
Beran

(10) Patent No.: US 8,614,873 B1
(45) Date of Patent: Dec. 24, 2013

(54) VARYING ELECTRICAL CURRENT AND/OR CONDUCTIVITY IN ELECTRICAL CURRENT CHANNELS

(76) Inventor: James T. Beran, Richmond, VA (US)

( * ) Notice: Subject to any disclaimer, the term of this patent is extended or adjusted under 35 U.S.C. 154(b) by 252 days.

(21) Appl. No.: 13/066,514

(22) Filed: Apr. 15, 2011

Related U.S. Application Data

(60) Provisional application No. 61/342,570, filed on Apr. 16, 2010.

(51) Int. Cl.
*H01H 47/00* (2006.01)

(52) U.S. Cl.
USPC .......................................................... 361/139

(58) Field of Classification Search
USPC .......................................................... 361/139
See application file for complete search history.

(56) References Cited

U.S. PATENT DOCUMENTS

| | | | |
|---|---|---|---|
| 3,021,459 A * | 2/1962 | Grubbs, Jr. et al. | 257/105 |
| 3,714,523 A | 1/1973 | Bate | |
| 4,163,986 A | 8/1979 | Vinal | |
| 4,467,296 A * | 8/1984 | Cohen et al. | 333/202 |
| 5,083,174 A | 1/1992 | Kub | |
| 5,208,477 A | 5/1993 | Kub | |
| 5,489,846 A | 2/1996 | Li et al. | |
| 5,528,067 A | 6/1996 | Farb | |
| 5,561,305 A | 10/1996 | Smith | |
| 5,742,077 A | 4/1998 | Patel et al. | |
| 5,747,859 A | 5/1998 | Mizushima et al. | |
| 5,757,055 A | 5/1998 | Kalb, Jr. | |
| 5,872,384 A * | 2/1999 | Gabara | 257/421 |
| 5,926,414 A * | 7/1999 | McDowell et al. | 365/170 |
| 6,744,250 B2 | 6/2004 | Hauenstein | |
| 7,012,276 B2 | 3/2006 | Kingsborough et al. | |
| 7,199,434 B2 | 4/2007 | Li et al. | |
| 7,319,261 B1 | 1/2008 | Power et al. | |
| 7,419,838 B2 | 9/2008 | Power et al. | |
| 7,435,229 B2 | 10/2008 | Wolf | |
| 7,605,399 B2 | 10/2009 | Kim et al. | |
| 7,666,751 B2 | 2/2010 | Marreiro et al. | |
| 7,687,891 B2 | 3/2010 | Schulze et al. | |

(Continued)

FOREIGN PATENT DOCUMENTS

JP 402194667 A 8/1990

OTHER PUBLICATIONS

Kuphaldt, T.R., Lessons in Electric Circuits, vol. IV—Digital, 2007, pp. 133-134.

(Continued)

*Primary Examiner* — Scott Bauer

(57) ABSTRACT

Electrical current and/or conductivity in an electrical current channel varies in response to spatiotemporal magnetic flux pattern and/or to variation in electromotive force (EMF). For example, a channel with time-varying electrical conductivity can have induced electrical current variation due to flux pattern resulting from electrical current in another channel or set of channels; the current variation can increase magnetic flux density. The electrical currents can be transient electrical currents, and can cascade to amplify a resulting electromagnetic waveform. A channel can include the channel of a zener or zener-like diode or of a transistor, as well as an extended conductive channel. Channels can be configured in electrical current loops and in various orientations and combinations to obtain current and/or conductivity variation. A transient electrical current can be triggered in a channel, e.g. by an EMF peak, and circuitry with a combination of EMF triggering components can perform logical and timing operation.

20 Claims, 10 Drawing Sheets

(56) References Cited

U.S. PATENT DOCUMENTS

| | | | |
|---|---|---|---|
| 7,710,329 | B2 | 5/2010 | Chiozzi |
| 7,948,045 | B2 | 5/2011 | Li et al. |
| 8,057,401 | B2 | 11/2011 | Wolf |
| 8,269,308 | B2 | 9/2012 | Lee et al. |
| 2006/0176624 | A1 | 8/2006 | Kuroda et al. |
| 2007/0167867 | A1* | 7/2007 | Wolf .............................. 600/561 |
| 2008/0070339 | A1* | 3/2008 | Power et al. ..................... 438/48 |
| 2008/0312719 | A1* | 12/2008 | Keilman .......................... 607/60 |

OTHER PUBLICATIONS

Boast, W.B. et al., "Electrical and Magnetic Circuits", in Fink, D.G. et al., Eds., Standard Handbook for Electrical Engineers, 14th Ed., New York: McGraw-Hill, 2000, pp. 2-1 to 2-8.

Boast, W.B. et al., "Electrical and Magnetic Circuits", in Fink, D.G. et al., Eds., Standard Handbook for Electrical Engineers, 12th Ed., New York: McGraw-Hill, 1987, pp. 2-1 to 2-3 and 2-10 to 2-16.

Sanders, R., "Researchers create first nanofluidic transistor, the basis of future chemical processors", berkeley.edu/news/media/release, Jun. 28, 2005, pp. 1-2.

Karnik, R., et al., "Electrostatic Control of Ions and Molecules in Nanofluidic Transistors", Nano Letters, vol. 5, No. 5, 2005, pp. 943-948.

Karnik, R., et al., "Effects of Biological Reactions and Modifications on Conductance of Nanofluidic Channels",,Nano Letters, vol. 5, No. 9, 2005, pp. 1638-1642.

Karnik, R., et al., "Field-effect control of protein transport in a nanofluidic transistor circuit", Applied Physics Letters, vol. 88, 2006, pp. 123114-1 to 123114-3.

Fan, R., et al., "Polarity Switching and Transient Responses in Single Nanotube Nanofluidic Transistors", Physical Review Letters, vol. 95, No. 8, 2005, pp. 086607-1 to 086607-4.

Itzler, M.A., et al., "InP-based Negative Feedback Avalanche Diodes", Proc. of SPIE, vol. 7222, 2009, pp. 72221K-1 to 72221K-12.

Jaworowicz, J., et al., "Magnetic logic using nanowires with perpendicular anisotropy", Nanotechnology, vol. 20, 2009, 215401, pp. 1-4.

Woolf, N.J., et al., Nanoneuroscience—Structural and Functional Roles of the Neuronal Cytoskeleton in Health and Disease, Heidelberg: Springer, 2009, pp. 177-178, 198-209, and 260-261.

"Electromagnetic Induction", wikipedia.com, downloaded Jun. 3, 2013, pp. 1-13.

"Transformer", wikipedia.com, downloaded Jun. 3, 2013, pp. 1-23.

Duckworth, H.E., Electricity and Magnetism, New York: Holt, Rinehart and Winston, 1960, pp. 230-239 and 377-381.

Lee, R., et al., Electronic Transformers and Circuits, Third Edition, New York: John Wiley & Sons, 1988, pp. 218-225 and 389-392.

Griffiths, D.J., Introduction to Electrodynamics, Englewood Cliffs, N.J.: Prentice-Hall, 1981, pp. 243-272.

\* cited by examiner

VARYING ELECTRICAL CURRENT AND/OR CONDUCTIVITY IN ELECTRICAL CURRENT CHANNELS

This application claims the benefit of U.S. Provisional Patent Application No. 61/342,570, filed Apr. 16, 2010, entitled "Inducing Electrical Current Variation in Channels", which is incorporated herein by reference in its entirety.

The techniques described herein involve variation in electrical current and/or conductivity in electrical current channels. Variation may result, for example, from spatiotemporal magnetic flux patterns or from variation in electromotive force (EMF).

Charge carrier current between source and drain of a field-effect transistor (FET) is sometimes described as flowing in a "channel", and many known techniques control conductivity of such a channel by varying voltage on a transistor's gate. Similar terminology has been adopted for other devices, such as nanofluidic transistors, in which movement of ions through a fluid-filled channel is similarly controlled by voltage on a transistor's gate.

U.S. Pat. No. 6,744,250 describes a sensor element based on trench MOS semiconductor technology; a vertical MOS channel of a trench MOSFET is used for sensing magnetic field: In presence of magnetic field, Lorentz force deflects moved charge carriers, thus increasing resistance in an MOS channel, leading to source-drain current change that may be used as a measure for magnetic field strength. In a multi-channel sensor chip, MOS channels along trench walls are all to be aligned parallel to one another, so that all channels run orthogonally with respect to linear magnetic-field direction.

It would be beneficial to have additional techniques for electrical current channels.

SUMMARY OF THE INVENTION

The invention provides several embodiments, including articles, methods of using, systems, and methods of making. In general, the embodiments involve varying electrical current and/or conductivity in electrical current channels.

These and other features and advantages will be understood from the figures and description.

DETAILED DESCRIPTION

Figure 1:
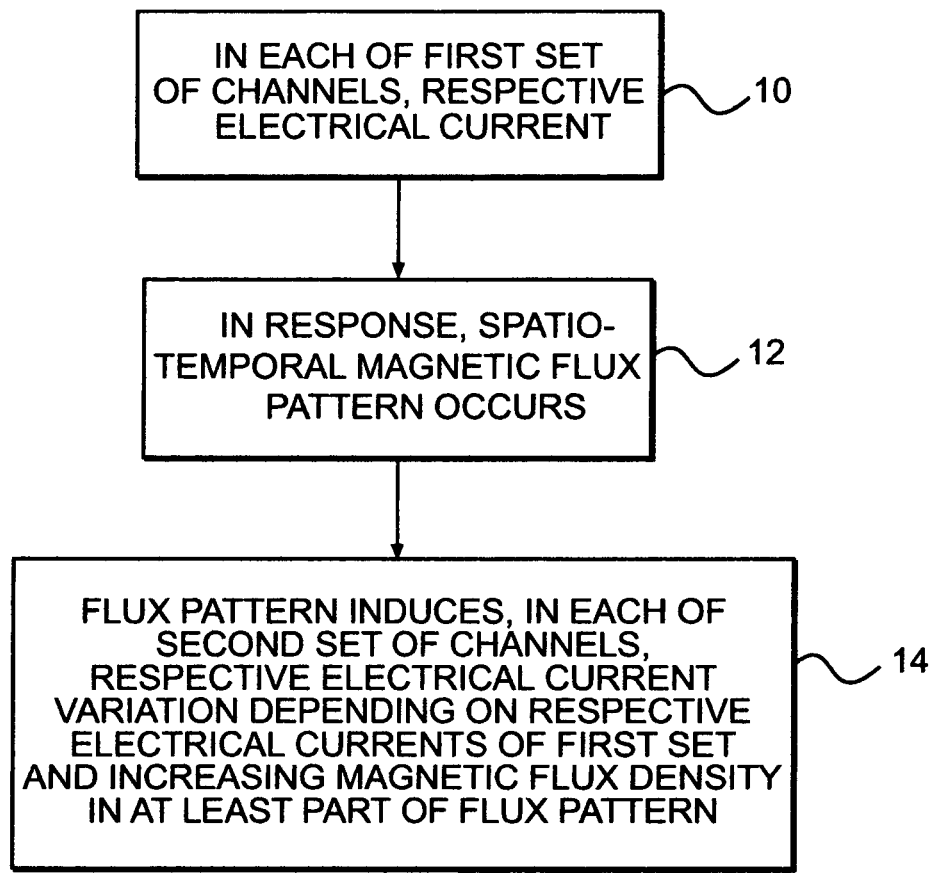
FIG. 1 is a flow chart showing events in which electrical current variation is induced in a set of one or more electrical current channels.

In the following detailed description, numeric values and ranges are provided for various aspects of the implementations described. These values and ranges are to be treated as examples only, and are not intended to limit the scope of the claims.

The term "electrical current channel", or simply "channel", is used herein to mean a region or a part of a physical structure or system in which electrical current can occur, such as through movement of electrons, holes, ions, or other charge carriers. Where consistent with the context, the term "channel" can include electrically conductive or semiconductive regions, but it is not limited to regions that fall within the usual meanings of "conductive" and "semiconductive". For example, the term "channel" can also include a region of plasma or vacuum in which ions can move, or a region in a fluidic, biological, or electrolytic structure or system within which ions can move.

A channel could be implemented in any of a multitude of ways, such as in a structure or system within which ions can move such as in a conductive material, a fluidic or biological channel, an electrolytic structure, or a plasma or vacuum region. Also, a channel could be implemented with semiconductive material through which charge carriers can move such as in a transistor or diode; semiconductor devices such as transistors and diodes can illustratively be described as having semiconductive channels with electrical conductivity that, in use, varies over time among a respective set of values that includes a substantially non-conductive value and at least one conductive value; an event causing a channel's transition from non-conductivity to conductivity is sometimes referred to as "activating" or "turning on" the channel, while an event causing a transition back to non-conductivity is sometimes referred to as "turning off" the channel. In addition to these possibilities, various other structural features or characteristics could support occurrence of electrical current in an electrical current channel.

The term "magnetic flux pattern", as used herein, includes any pattern of magnetic flux, also sometimes referred to as a magnetic field. The more specific term "spatiotemporal magnetic flux pattern" refers to a magnetic flux pattern that varies both in space and in time.

The term "inductive coupling" is used herein to refer to a relation between two or more electrical currents that can be modeled as if some of the currents were induced by magnetic flux pattern or electromotive force (EMF) caused by others of the currents; for such a modeling to succeed, the context must be consistent with induction by magnetic flux pattern or EMF, where EMF has magnitude that equals or approximates a first time derivative of magnetic flux density.

As used herein, a current or current variation is "induced" in any case in which the current or current variation results from inductive coupling between electrical currents in first and second sets of one or more channels each, where the inductive coupling is via a magnetic flux pattern and/or EMF and where the second set includes at least one channel that is not in the first set.

The terms "configured" and "configuration", when used herein relative to channels and other features, refer to combinations of characteristics such as position, shape, size, orientation, grouping, material, electrical conductivity and/or resistivity, and so forth, that achieve specified functional or other results or meet functional or other criteria; for example, a configuration may include a combination of channel shapes and relative positions such that inductive coupling occurs between electrical currents in the channels. In a configuration in which change can occur over time, such as through relative motion between channels, the terms "configured" and "configuration" can include a combination of such characteristics that changes over time.

A "coupling group" of channels includes, for example, a group of channels configured such that, in use, inductive coupling occurs between electrical currents in the coupling group. Configuration of a group of channels could include not only geometrical, material, and electrical features of each channel and geometrical relations of the channels, but also material features of a region around the channels, such as magnetic characteristics of material(s) in the region.

Previously available techniques for interactions between channels and magnetic flux patterns or variations in EMF are limited. Exemplary implementations described herein address this problem. More specifically some exemplary implementations address the additional problem of inducing electrical current variation that increases magnetic flux density in a spatiotemporal magnetic flux pattern; other exemplary implementations address additional problems of varying conductivity in response to variation in EMF and of triggering a transient electrical current.

Unless the context indicates otherwise, the terms "circuitry" and "circuit" are used herein to refer to structures in which one or more components have sufficient electrical and/or magnetic connections to operate together or in a related manner. In some instances, an item of circuitry can include more than one circuit. An item of circuitry that includes a "processor" may sometimes be analyzed into "hardware" and "software" components; in this context, "software" refers to stored or transmitted data that controls operation of the processor or that is accessed by the processor while operating, and "hardware" refers to components that store, transmit, and operate on the data. The distinction between "software" and "hardware" is not always clearcut, however, because some components share characteristics of both; also, a given software component can often be replaced by an equivalent hardware component without significantly changing operation of circuitry.

Some implementations described below involve a "system", used herein to mean a combination of two or more parts or components, such as processing components and other components, that can perform a function together.

The flow chart in FIG. 1 illustrates events that can occur in implementations described herein. In box 10, an operation is performed that produces, causes, or otherwise results in a respective electrical current in each of a first set of channels. As explained in greater detail below, the first set of channels are included in a number of channels configured so that the events in boxes 12 and 14 also occur.

Box 12 shows that, in response to the respective electrical currents in box 10, a spatiotemporal magnetic flux pattern occurs. Box 14 shows that the flux pattern induces, in each of a second set of the channels, a respective electrical current variation that depends on the respective electrical currents in box 10 and that also increases the magnetic flux density in at least part of the spatiotemporal flux pattern. For example, at least some information from the respective electrical currents in box 10 could be transferred to the respective electrical current variation in box 14, such as information about timing, direction, or magnitude of the respective electrical currents; in some implementations, the flux pattern could in effect "trigger" the respective electrical current variation in box 14, such as by causing a current in a channel that had previously been non-conductive; in other implementations, the flux pattern could cause a change in timing, direction, or magnitude of a current that had previously existed in a conductive channel. Also, for example, magnetic flux density in at least a part of a flux pattern could increase in magnitude due to superposition of magnetic flux density from the respective electrical currents in the first and second sets of channels, where the superposed magnitude is greater as a result of the induced electrical current variation.

In general, the operation in box 10 could be performed by any system, circuitry, or other component capable of producing, causing, or otherwise resulting in the respective electrical currents in the first set of channels. In implementations described below, the respective electrical currents are generally produced or caused, but it is conceivable that the respective electrical currents could result from an uncontrolled stimulus, such as a stimulus being measured.

The operation in box 10 and the events in boxes 12 and 14 could be implemented in numerous ways with a wide variety of channels in any of a variety of configurations. Several exemplary implementations are described below.

Figure 2:
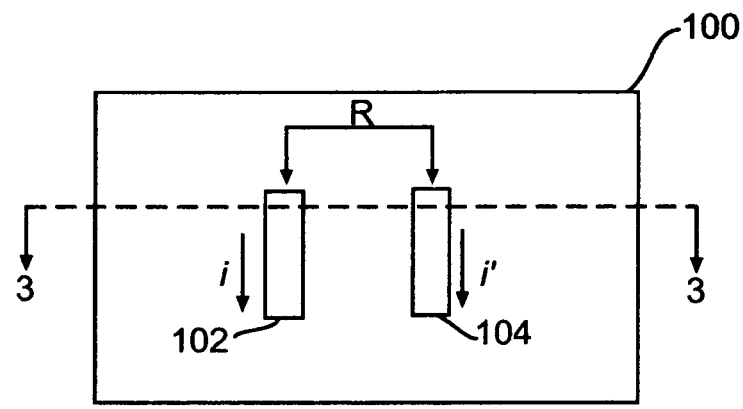
FIG. 2 is a schematic diagram of an item that includes first and second electrical current channels.

FIG. 2 shows item 100, which could, for example, be a device, an article of manufacture, or a component of a system. Item 100 includes channels 102 and 104, with channel 102 illustratively being a first set of one or more channels and channel 104 illustratively being a second set of one or more channels. Channels 102 and 104 are illustratively parallel or approximately parallel, with central axes that are separated by approximately distance R, an example of how channels can be configured. Electrical current variation i' is induced in channel 104 via a spatiotemporal magnetic flux pattern in response to current i produced, caused, or otherwise resulting in channel 102.

Figure 3:
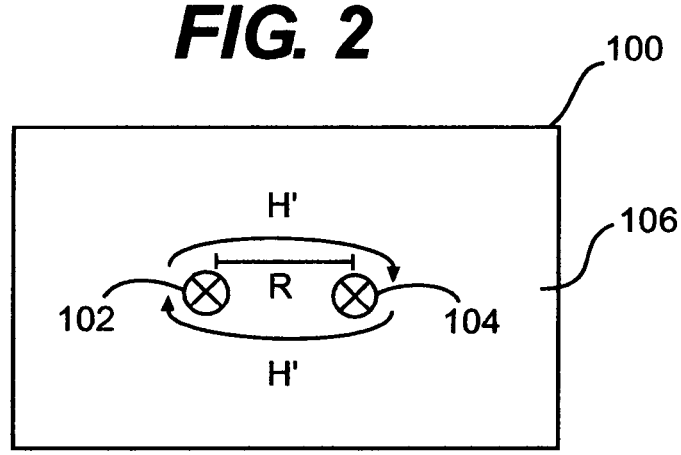
FIG. 3 is a cross-sectional view of the item of FIG. 2, taken along the line 3-3 in FIG. 2.

FIG. 3 shows a cross section of item 100 along the line 3-3 in FIG. 2. The arrows labeled H' illustrate the spatiotemporal magnetic flux pattern in response to current in channel 102. Also, region 106 around channels 102 and 104 has material features such that, in addition to other features of item 100, at least part of the magnetic flux density increases as a result of electrical current variation i'. It is possible, for example, that channel 104 might have a bias current, and that the bias current increases in magnitude in response to the magnetic flux pattern, causing magnetic flux density to increase in at least part of the spatiotemporal flux pattern.

Figure 4:
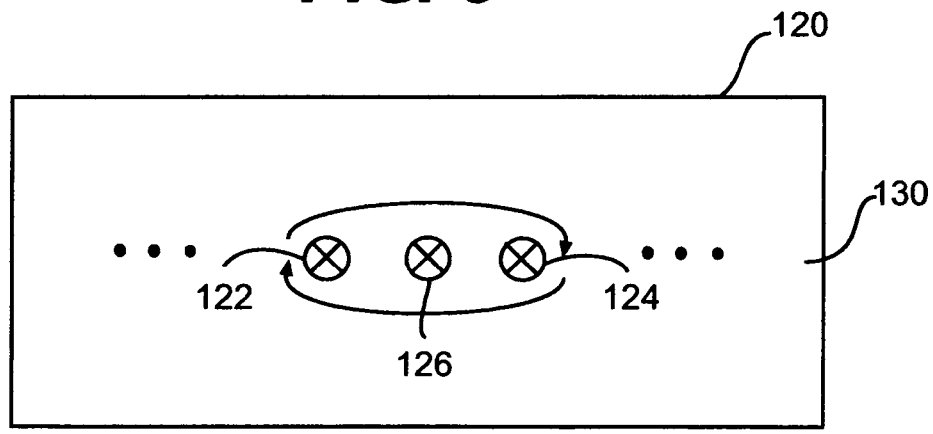
FIG. 4 is a cross-sectional view similar to that in FIG. 3, but for an item with an array of three or more electrical current channels.

FIG. 4 shows a cross section of item 120 taken from a viewpoint similar to that of FIG. 3. Item 120 could, for example, include an array of approximately parallel channels on a surface of a substrate, with three channels in the array being illustratively shown. Channels 122 and 124 are illustratively in a first set of channels and channel 126 is illustratively in a second set of channels. In response to respective electrical currents produced, caused, or otherwise resulting in channels 122 and 124, electrical current variation is induced in channel 126 via a spatiotemporal magnetic flux pattern. Region 130 around the channels again has material features such that, in addition to other features of item 120, at least part of the magnetic flux density increases as a result of electrical current variation in channel 126.

Figure 5:
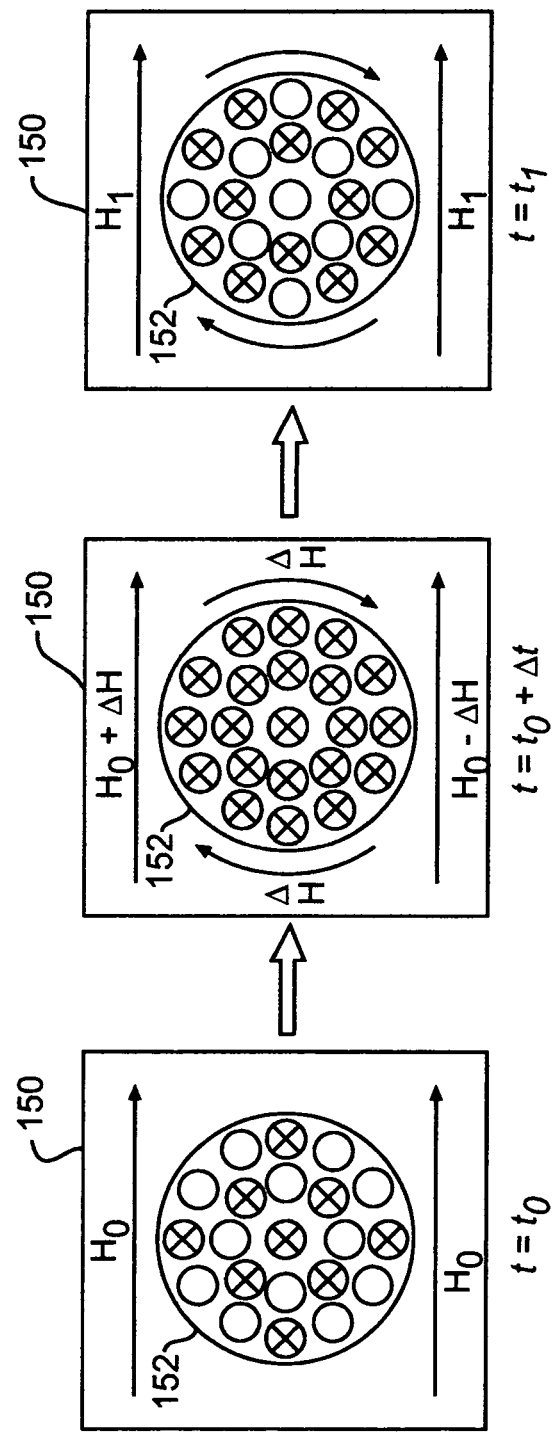
FIG. 5 shows a sequence of cross-sectional views similar to that in FIG. 3, but for an item with a three-dimensional arrangement of electrical current channels.

FIG. 5 shows a sequence of three cross-sectional views of item 150 taken from a viewpoint also similar to that of FIG. 3. Item 150 illustratively includes a three-dimensional arrangement 152 of approximately parallel channels, configured, for example, in a shape similar to that of a column; a three-dimensional arrangement as shown might, for example, be implemented in patterned layers over a substrate, such as thin films or organic layers. In the first view, at left in FIG. 5, at time $t_0$, each of a first set of the channels in arrangement 152 has a respective electrical current, and there is a biasing or surrounding magnetic field $H_0$. At time $t_0 + \Delta t$, shown in the second view at center in FIG. 5, electrical current has been induced in a second set of the channels, and the magnetic flux density around arrangement 152 is increased, as indicated by the arrows labeled $\Delta H$. Therefore, the resulting magnetic field ranges depending on position from $H_0 + \Delta H$ to $H_0 - \Delta H$, as shown. Finally, at time $t_1$, shown in the third view at right in FIG. 5, electrical current has ceased flowing in the first set of channels but continues to flow in the second set, resulting in magnetic field $H_1$ as shown. This suggests how a measurement might be made based on the remaining current in the second set of channels.

Figure 6:
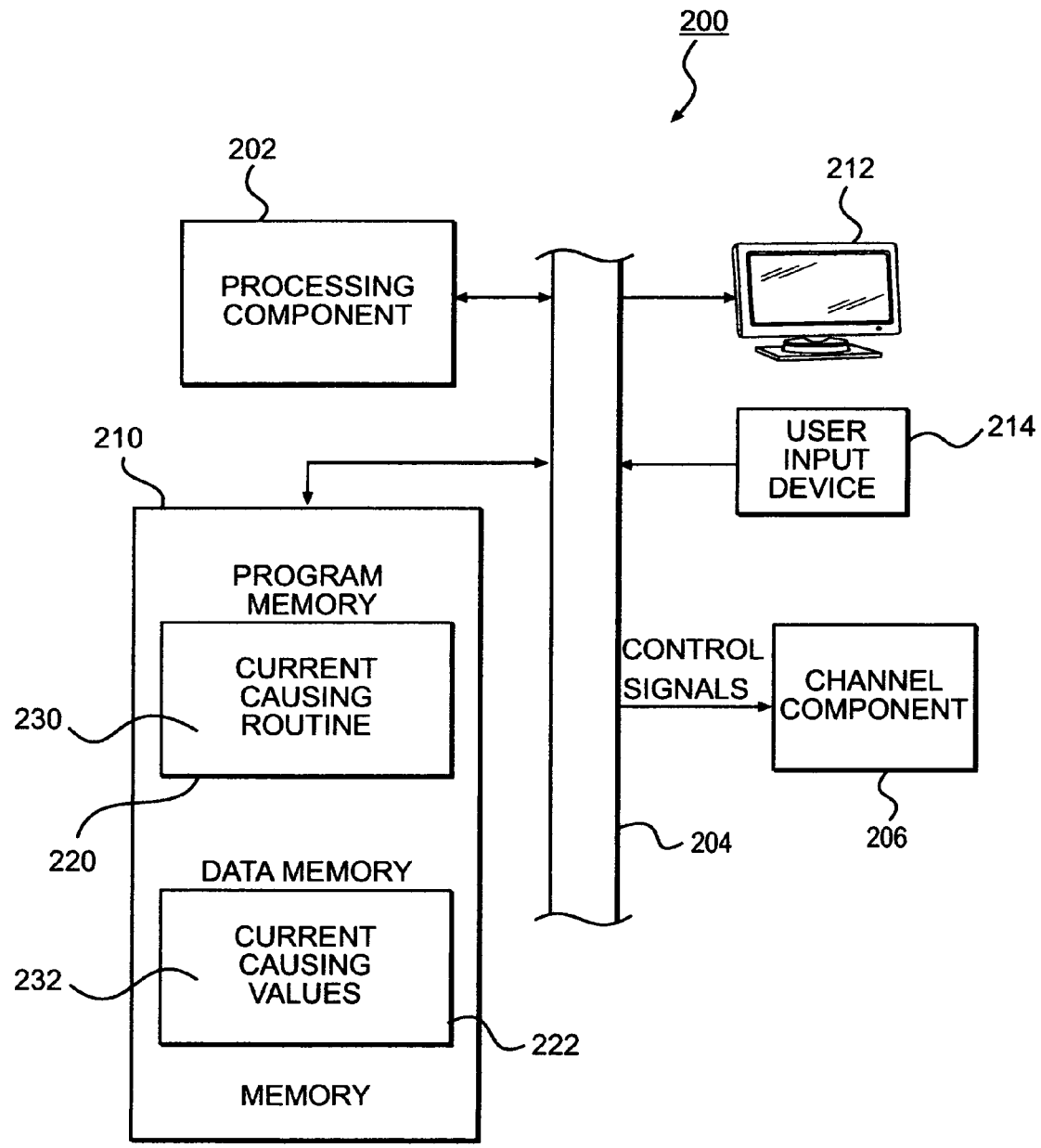
FIG. 6 is a schematic diagram of an exemplary system in which events as in FIG. 1 could occur.

FIG. 6 is a schematic diagram of system 200, one of a variety of data processing systems in which events as in FIG. 1 could occur. Unless the context indicates otherwise, the term "data" is used herein to refer to signals in digital form, such as binary data. The term "data structure" refers to a combination of items of data that are ordered, linked, associated such as in a table, or otherwise related such that some items in the combination can be accessed based on other items; although exemplary data structures are described below as stored in memory, a data structure can take other forms, such as during transmission through a data communication network.

FIG. 6 illustrates general features of an implementation with processing component 202, e.g. including one or more central processing units (CPUs) connected to other components through bus 204, but connecting circuitry and other features as described herein could be implemented in many other architectures. Furthermore, any suitable processing component and bus architecture could be used to implement system 200.

In the illustrated example, bus 204 also connects to channel component 206, which could be implemented in any of the ways described herein, and to memory 210, display 212, and user input device 214, which could, for example, include a keyboard and a mouse. Bus 204 could also connect to various other I/O devices.

Memory 210 could be implemented with any suitable combination of memory devices, including drives for storage and retrieval of information from storage media, such as magnetic or optical media. Processing component 202 or another processor could perform memory management using any suitable technique.

Memory 210 illustratively includes program memory 220 and data memory 222, implemented in any suitable way. In addition to various other software, program memory 220 illustratively includes current causing routine 230 and data memory 222 illustratively includes current causing values 232, which could be implemented as a data structure. Routine 230 could, for example, implement the operation in box 10 in FIG. 1, accessing current causing values 232 to obtain any appropriate parameters used in the operation; in performing the operation by executing routine 230, processing component 202 could provide control signals through bus 204 (or other connecting circuitry) to channel component 206, causing the respective electrical currents and the events in boxes 12 and 14 in FIG. 1 as described above. In general, software components could alternatively be implemented as hardware components or with a combination of software and hardware, and some hardware components could similarly be implemented in software.

Techniques as described above offer the possibility of a wider variety of interactions between channels and magnetic flux patterns. In particular, they can be used to induce electrical current variation that increases magnetic flux density in a spatiotemporal magnetic flux pattern. In addition, as explained in more detail below, they can be implemented in devices with conductivity that varies in response to EMF variation and in which transient electrical currents are triggered.

Principles developed in relation to transformers are helpful in understanding some exemplary implementations described herein: A simple transformer includes a primary coil and a secondary coil; electrical current in the primary coil results in magnetic flux density, and change in magnetic flux density over time in turn results in electrical current in the secondary coil, with the current's direction opposing the time change in the magnetic flux density. The term "transformer electromotive force", abbreviated "transformer EMF", is used herein to describe EMF that results from change in magnetic flux density in a transformer and that can also cause current to flow in a transformer's secondary coil.

According to standard treatments, transformer EMF magnitude is proportional to the first time derivative of magnetic flux density. Therefore, if magnitude of magnetic flux density proportionally follows a sinusoidal primary current, transformer EMF would also be sinusoidal. The transformer EMF therefore causes or "induces" a sinusoidal secondary current with the same frequency as the primary current. Primary and secondary currents related in this way are examples of electrical currents that are "inductively coupled" as that term is explained above.

Exemplary implementations can accordingly include first and second (and possibly more than two) sets of channels configured such that a synchronized, time-varying electrical current in the first set of channels ("primary current") can cause a synchronized, time-varying electrical current in the second set of channels ("secondary current"). When the relation between primary current and secondary current can be modeled as if the secondary current were induced by EMF resulting from the primary current, the two sets of channels are referred to as "inductively coupled". In general, such implementations can employ various configurations, such as with various channel conductivity characteristics and various flux patterning characteristics, e.g. with the magnetic circuit that relates the primary and secondary channels having any suitable permeance, reluctance, etc.

Although primary and secondary currents in a transformer are typically sinusoidal, sinusoidal currents are not the only example of currents that can be inductively coupled. Of particular interest for this application are exemplary implementations in which electrical current in a set of primary channels can be modeled as causing EMF to rapidly rise to a peak at which it has a maximum magnitude, with such a peak sometimes referred to herein as an "EMF peak". Rather than being sinusoidal or steady state in some way, electrical currents that can be modeled as causing EMF peaks are more likely to be transient; a typical example described below is a transient electrical current that rapidly rises to a peak and then falls from the peak along an exponential or approximately exponential decay curve.

An EMF peak can, in turn, be modeled as activating or turning on a secondary channel. If, when turned on, the secondary channel responds with an electrical current, this would be another example of inductive coupling. In this example, the induced electrical current might similarly be transient, rapidly rising to a peak and then falling from the peak, or it could in other cases be a steady state current that remains approximately constant after the secondary channel is turned on.

A channel turned on by an EMF peak could also be an example of "channel triggering", used herein as a generally category of phenomena in which a channel responds shortly after onset of a stimulus ("triggering event") with an electrical current of relatively long duration ("triggered current"); in exemplary implementations, a triggered current's duration might be measured, e.g., from its onset through its peak and down to half its peak maximum, and its duration might be more than twice the time between onset of the triggering event and onset of the triggered current. A channel that responds to activation by an EMF peak with a triggered current is sometimes referred to herein as an "EMF triggering channel". In the special case where the triggered current is transient and provides or contributes to a further EMF peak that triggers one or more further channels to provide triggered currents, the sequence of triggerings may be described herein as an "EMF triggering cascade"; for an EMF triggering cascade to continue, a set of concurrent transient electrical currents must have sufficient peak magnitudes and appropriate decay curves to produce an EMF peak capable of being a triggering event for further channels.

Figure 7:
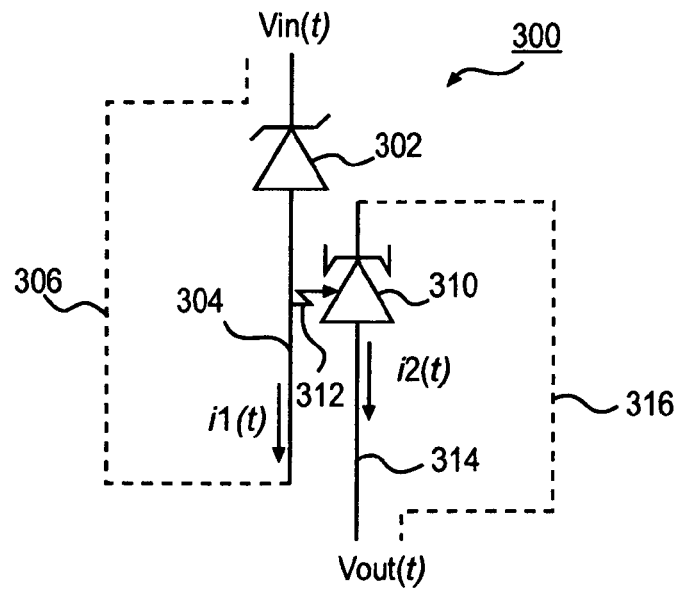
FIG. 7 is a schematic circuit diagram of a device in which a transient electrical current in an extended conductive channel triggers a transient electrical current in an electromotive force (EMF) triggering diode.

FIG. 7 shows a schematic circuit diagram of device 300, a simple exemplary implementation of techniques described herein. Within device 300, zener diode 302, extended conductive channel 304 (solid line), and return conductive line 306 (dashed line) are electrically connected so that a voltage Vin(t) can be received between diode 302 and line 306; diode 302 is biased by appropriate biasing circuitry (not shown) so that, if Vin(t) exceeds the breakdown voltage of diode 302, a transient electrical current $i1(t)$ flows in channel 304. It should be noted, however, that return line 306 may not be an identifiable electrical component within or external to device 300, but may instead exist only through common or ground connections, through connections to electrolytic fluid, etc. The term "extended conductive channel", illustratively applied to channel 304, is used herein to refer to a channel that is conductive and that is sufficiently longer in a length direction than it is wide in any direction perpendicular to the length direction at any point along the length direction so that it produces a magnetic flux pattern similar in orientation to what would be produced by a thin linear conductor of infinite length, i.e. a magnetic flux pattern that obeys the right-hand rule; it is expected that, for most implementations, a length/width ratio of two, five, ten, or twenty would be sufficient to produce such a magnetic flux pattern, depending on other characteristics of the configuration; further, the length direction need not extend in a straight line, but could, for example, include one or more curves, bends, or other departures from straightness, provided the magnetic flux pattern obeys the right-hand rule.

Device 300 also includes EMF triggering component 310, which could be implemented, for example, as a zener-like diode and therefore is shown with a symbol similar to a zener diode; this same symbol is used in other figures to represent other EMF triggering components. Component 310 is electrically connected to extended conductive channel 314 (solid line) at one lead and to return conductive line 316 (dashed line) at the other, so that, when suitably biased by biasing circuitry (not shown), component 310 responds to an EMF pulse (represented by arrow 312) of sufficient magnitude and appropriate direction by providing, due to avalanche effects, a transient electrical current $i2(t)$ in channel 314. Also, voltage Vout(t) may be provided as an output voltage, between channel 314 and line 316. As with line 306, return line 316 may not be an identifiable electrical component within or external to device 300, but may instead exist only through common or ground connections, through connections to electrolytic fluid, etc. As discussed in greater detail below, however, it may be beneficial in some exemplary implementations for component 310, channel 314, and line 316 to form a closed loop around which EMF is defined. Also, as will be understood from the above definitions, channel 314 and a portion of component 310 that becomes conductive in response to an EMF pulse together come within the definition of "channel" as used herein.

Figure 8:
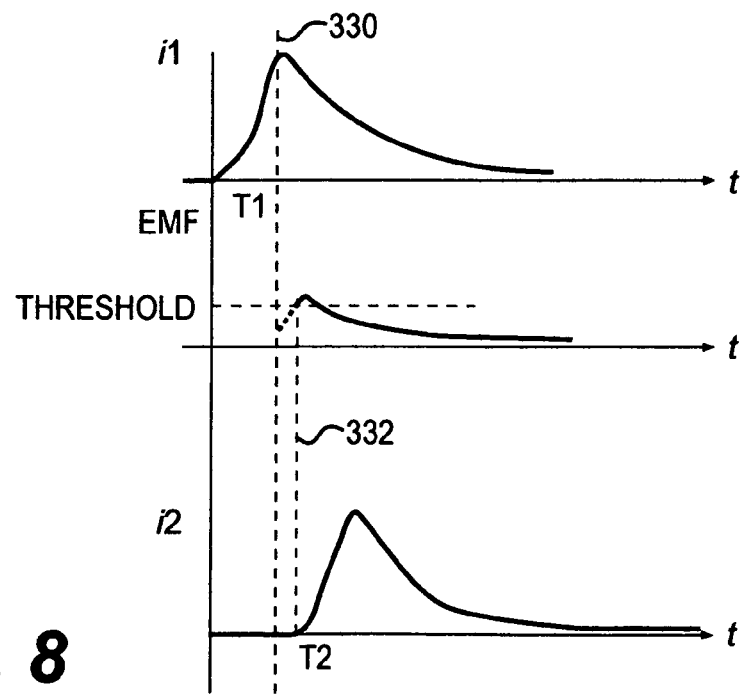
FIG. 8 shows graphs of primary current, EMF, and secondary current over time as expected in the device of FIG. 7.

FIG. 8 illustrates general features of $i1(t)$, $i2(t)$, and the EMF represented by arrow 312. The horizontal axis of all three graphs is a time axis, with the vertical axis being at the time at which voltage Vin(t) exceeds the breakdown voltage of diode 302.

In the upper graph in FIG. 8, i1 rises rapidly to its peak magnitude, which occurs at a time T1 indicated by dashed line 330. After reaching its peak magnitude, i1 decays exponentially or approximately exponentially; in other words, i1 is an example of a transient electrical current. One possible way to achieve a transient electrical current would be to connect an appropriate capacitive component (not shown) across zener diode 302 and to connect a time-varying current source (not shown) to the input node of zener diode 302 and the capacitive component; while the voltage across the capacitive component remains below the breakdown voltage of diode 302, the capacitive component will receive charge carriers from the current source, increasing its voltage until breakdown voltage is reached, at which time a channel at the p-n junction of diode 302 becomes conductive due to avalanche effects, and the capacitive component will discharge through diode 302 along a curve resembling i1 in FIG. 8.

The second graph in FIG. 8 shows EMF magnitude, such as in EMF triggering component 310. If magnetic flux were proportional to i1, it follows from Faraday's Law of Induction that EMF would approximate the negative of the first derivative of magnetic flux, initially going to a negative peak (not shown), then rising to cross the horizontal axis at approximately time T1, represented by vertical dashed line 330; the portion of EMF just prior to T1 is shown, however, as a dashed line to indicate that the actual EMF curve might not take precisely this course, depending on the configuration of device 300. After crossing the horizontal axis, EMF then illustratively rises further toward a positive peak; before reaching the positive peak, however, EMF reaches a threshold value at time T2, represented by vertical dashed line 332. Due to appropriate biasing, EMF triggering component 310 responds after time T2 by providing transient electrical current i2, which is an example of a triggered current as explained above, because it has relatively long duration measured from its onset through its peak and down to half its peak maximum; if time T1 is treated as onset of the triggering event, the duration of current i2 measured in this way might be more than twice the time between T1 and onset of the triggered current at time T2. If component 310 is similar to a zener diode, for example, current i2 could result from avalanche effects. Current i2 could, in turn, have an effect on EMF, but FIG. 8 does not show this effect.

As used herein, the term "spatiotemporal electromagnetic waveform", or more simply "spatiotemporal EM waveform" or just "EM waveform", refers to a combination of electric and magnetic fields that varies in both space and time. Each of currents i1 and i2, if it occurred by itself without the other, would have a respective spatiotemporal electromagnetic waveform (i.e. EM waveform), in particular including magnetic field that varies in both space and time. On the other hand, the EM waveform resulting from current i1 and the EM waveform resulting from current i2 could interact: For example, if the elapsed time between T1 and T2 is sufficiently short, if channels 304 and 314 and other components of device 300 are appropriately configured, and if other applicable constraints necessary for operation of device 300 in this manner are met, greater combined EM waveform magnitude could occur than would result from either of currents i1 and i2 by itself. As discussed below in relation to exemplary implementations, this could result in a type of amplification, in this case amplification of current i1.

It is believed that EMF triggering component 310 could be implemented in a variety of ways. A relatively straightforward implementation would be a zener-like diode biased by appropriate circuitry (not shown) so that EMF at threshold causes charge carrier avalanche to occur in its channel, just as voltage exceeding breakdown voltage would do. Other variations could include FET-like channels that become conductive in response to EMF at threshold; U.S. Pat. No. 7,065,399 describes thin film transistor (TFT) techniques that might be used to implement such channels, and is incorporated herein by reference in its entirety. Further, component 310 could include a combination of such items, e.g. one or more zener-like diodes and one or more FET-like channels, connected in parallel or in another appropriate configuration to result in a desired response to EMF resulting from a spatiotemporal EM waveform.

It would also be possible to implement zener diode 300 in a variety of ways, or to replace it with another component that could be turned on to provide a transient electrical current. For example, diode 300 might be replaced by a TFT or other transistor that is appropriately connected to other circuitry so that it provides a transient electrical current when turned on by an appropriate gate voltage.

Figure 9:
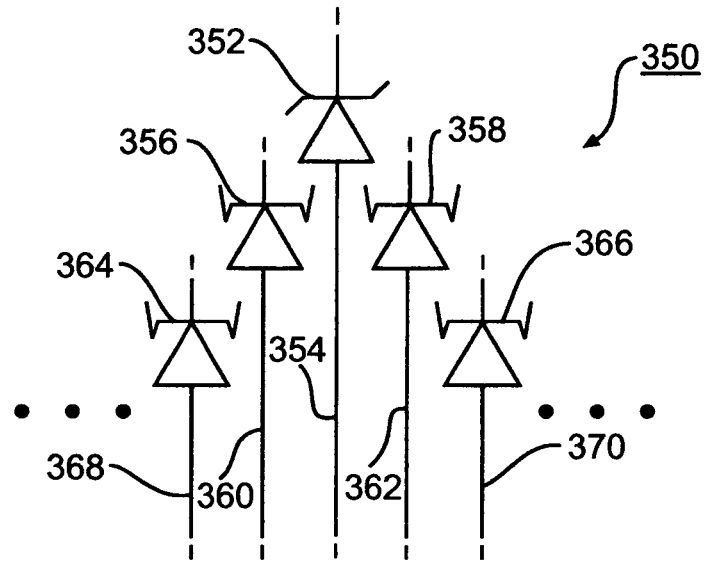
FIG. 9 is a schematic circuit diagram of a device in which an EMF triggering cascade can occur.

In addition to addressing problems set forth above, the technique of FIG. 9 addresses problems in amplifying transient electrical currents, alleviating such problems with a cascading approach. FIG. 9 shows a schematic circuit diagram of device 350, illustrating a simple exemplary implementation in which cascading can occur. Zener diode 352 is connected to extended conductive channel 354 and is connected to other appropriate circuitry (not shown) for biasing and other purposes, so that channel 354 carries a transient electrical current when diode 352 receives a voltage exceeding its breakdown voltage. The channel of diode 352 and channel 354 together can serve as a channel in a first set.

Along channel 354 are EMF triggering components 356 and 358, configured so that they receive EMF from transient electrical current in channel 354 and connected to other appropriate circuitry (not shown) for biasing, etc. In response to an EMF peak due to transient electrical current in channel 354, each of components 356 and 358 provides a respective transient electrical current to its respective extended conductive channel 360 or 362. The channels of components 356 and 358, each forming a channel together with its respective conductive channel 360 or 362, can serve as channels in a second set.

Along channels 360 and 362 are EMF triggering components 364 and 366, respectively, configured so that they receive EMF from transient electrical current in channels 360 and 362, respectively, and connected to other appropriate circuitry (not shown) for biasing, etc. In response to transient electrical current in the respective one of channels 360 and 362, each of components 364 and 366 provides a respective transient electrical current to its respective extended conductive channel 368 or 370. The channels of components 364 and 366, each forming a channel together with its respective conductive channel 368 or 370, can serve as channels in a second set.

As suggested by the ellipses at left and right in FIG. 9, further EMF triggering components could provide transient electrical currents in response to transient electrical currents in channels 368 and 370, and so forth. Also, a larger cascade effect could be obtained by providing additional EMF triggering components and extended conductive channels. As will be understood, a cascade effect may amplify an EM waveform from a primary transient electrical current, because it results in multiple transient electrical currents, each of which may contribute to the EM waveform in the manner suggested in FIG. 8; this effect can be understood, for example, by taking a sum of magnitudes of the separate waveforms of currents i1 and i2 in FIG. 8. If the cascade effect has a sufficiently high growth rate per stage, i.e. for each stage, the number of EMF triggering components that are triggered by each transient electrical current in an extended conductive channel, and if the rate of exponential decay of the transient electrical currents has a sufficiently long time constant, the combined EM waveform's magnitude should grow with the cascade effect until a peak magnitude or amplitude is reached, after which the EM waveform's magnitude should decay. It may be possible to obtain higher growth rates per stage with three dimensional implementations, along lines described below. Further, a series of iterations could be performed to obtain a series of amplified EM waveforms, each due to cascading and with each amplified peak followed by a valley of sufficient duration so that another peak can be provided by the next iteration; a series of cycles of such amplified peaks could be used, such as in a context in which a signal of at least a minimum duration is required to make a transition between one operation and another.

Figure 10:
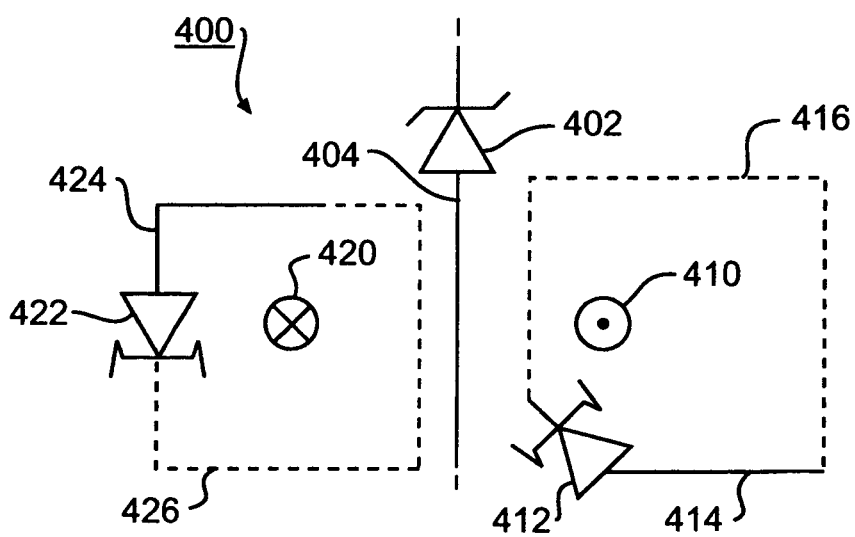
FIG. 10 is a schematic circuit diagram of a device in which EMF triggering diodes in loops can be triggered.

FIG. 10 shows a schematic circuit diagram of device 400, illustrating another simple exemplary implementation that employs closed current loops, analogous to secondary coils of a transformer. Zener diode 402 is connected to extended conductive channel 404 and is connected to other appropriate circuitry (not shown) for biasing and other purposes, so that channel 404 carries a transient electrical current when diode 402 receives a voltage exceeding its breakdown voltage.

As indicated by arrowhead 410, the transient electrical current results in magnetic flux in accordance with the right hand rule. In the illustrated example, the magnetic flux passes through a closed current loop through EMF triggering component 412, extended conductive channel 414 (solid line), and return line 416 (dashed line), resulting in EMF along the closed current loop in accordance with Faraday's law. If component 412 is appropriately biased by circuitry (not shown) and if it, channel 414, and return line 416 are appropriately configured relative to channel 404, component 412 will be triggered by the EMF, and, in response, will provide a transient electrical current to channel 414.

Similarly, as indicated by arrow tail 420, magnetic flux in accordance with the right hand rule passes through another closed current loop on the opposite side of channel 404, this time through EMF triggering component 422, extended conductive channel 424 (solid line), and return line 426 (dashed line), again resulting in EMF along the closed current loop. As above, if component 422 is appropriately biased by circuitry (not shown) and if it, channel 424, and return line 426 are appropriately configured relative to channel 404, component 422 will be triggered by the EMF, and, in response, will provide a transient electrical current to channel 424.

Techniques as in FIGS. 9 and 10 could be implemented separately or together. If used together, it may be possible to obtain cascade effects with a wide variety of geometries in addition to the parallel geometry of FIG. 9.

Figure 11:
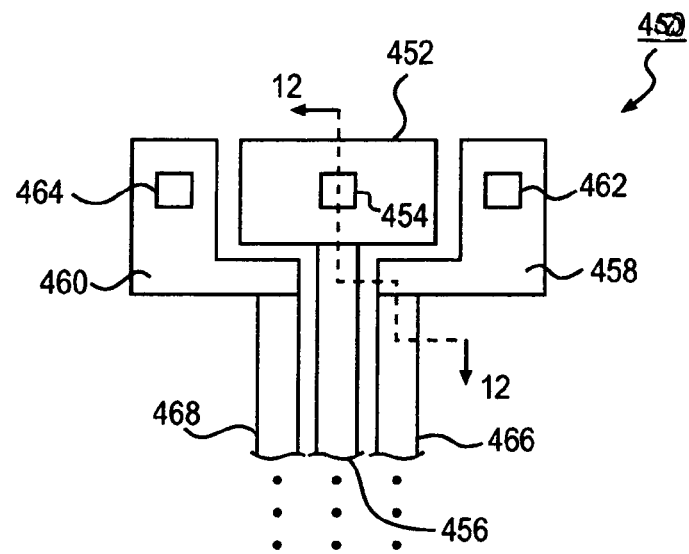
FIG. 11 is a schematic top view of a partial layout of an exemplary thin film device that would implement components similar to some of those in FIG. 9.

FIG. 11 shows a partial layout of thin film device 450, an exemplary thin film device that would implement components similar to some of those in FIG. 9. In the illustrated partial layout, device 450 is left-right laterally symmetrical, so that description of one side applies to the other side in mirror image.

Lead 452 is a first lead of a zener diode that can be connected to biasing and input voltages through metal contact 454. Lead 456 is a second lead of the zener diode, and is also an extended conductive channel that can be connected to a return line (not shown) similar to features shown in FIGS. 7 and 10.

Leads 458 and 460 are first leads of first and second zener-like EMF triggering diodes, respectively, and can be connected to biasing voltages through metal contacts 462 and 464, respectively. Leads 466 and 468 are second leads of the first and second zener-like EMF triggering diodes, respectively, and are also extended conductive channels that can be connected to respective return lines (not shown) similar to features shown in FIGS. 7 and 10.

Figure 12:
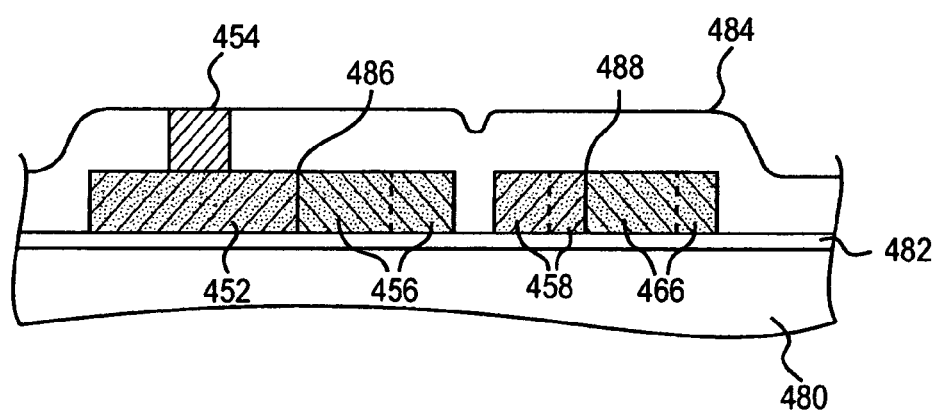
FIG. 12 is a cross-section of an exemplary thin film device implementation taken along line 12-12 in FIG. 11.

FIG. 12 is a cross-section of an exemplary thin film device implementation taken along line 12-12 in FIG. 11. Solid vertical lines in the cross section represent boundaries between regions that differ, e.g. in material or doping, while dashed vertical lines represent bends in line 12-12, with the same region being on both sides of each such bend.

The illustrated implementation could be fabricated by depositing and/or patterning thin films over substrate 480, which could be any appropriate substrate including, for example, an intrinsic semiconductor such as silicon, sapphire, an insulator, or etc. For some implementations, a barrier layer or other layer for insulation, protection, or the like is beneficial, as indicated by layer 482 on substrate 480. Further layers (not shown) could also be formed over substrate 480 before producing device 450.

As shown at left in FIG. 12, first lead 452 extends laterally under and supports metal contact 454, which extends through layer 484, another layer for insulation, protection, and the like, which can be formed, e.g. from a semiconductor oxide or other non-conductive material. In organic implementations, layer 484 could be a suitable insulating polymer. To the right of first lead 452 is second lead 456. The two leads 452 and 456 are semiconductive but oppositely doped, and meet at junction 486, the p-n junction of the zener diode.

To the right of second lead 456 is first lead 458 of one of the zener-like EMF triggering diodes in device 450, i.e. the one at the right in FIG. 11. Between second lead 456 and first lead 458, layer 484 extends down to layer 482, insulating the leads of the two components from each other. To the right of first lead 458 is second lead 466. As with the zener diode described above, the two leads 458 and 466 are semiconductive but oppositely doped, and meet at junction 488, the p-n junction of the zener-like EMF triggering diode.

Device 450 could be fabricated as shown in FIG. 12 in various ways, such as using photolithographic techniques, ink jet printing techniques, or other suitable microfabrication techniques. Forms of silicon and silicon oxides, for example, could be deposited, patterned, and/or doped to produce parts other than metal contacts. Or organic semiconductors, conductors, and insulators could be deposited, patterned, and/or doped to produce such parts.

Figure 13:
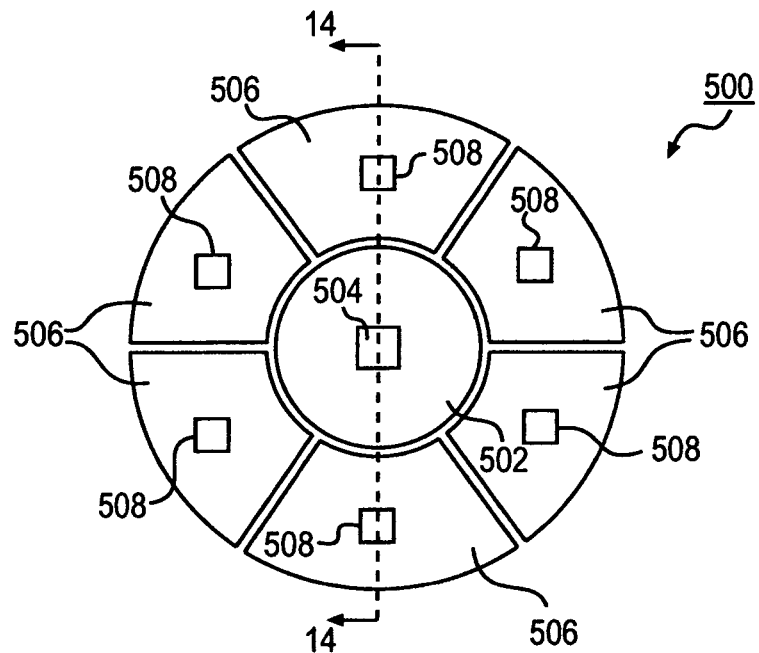
FIG. 13 is a schematic top view of an exemplary three-dimensional layout that would implement components similar to some of those in FIG. 9.

Similarly to FIG. 11, FIG. 13 shows a partial layout of three-dimensional (3D) device 500, another exemplary device that would implement components similar to some of those in FIG. 9. In the illustrated partial layout, device 500 is approximately side-to-side radially symmetrical about a central axis, so that description of one side of any cross-section through the central axis applies to the other side approximately in mirror image.

Lead 502 is a first lead of a zener diode that can be connected to biasing and input voltages through conductive contact 504. Around the zener diode are configured six zener-like EMF triggering diodes in a circle, with each triggering diode having a first lead 506 that can be connected to biasing voltage through a respective conductive contact 508. As can be understood from FIG. 13, further concentric (or nonconcentric) circles of zener-like EMF triggering diodes could be configured around the illustrated circle of six triggering diodes.

Figure 14:
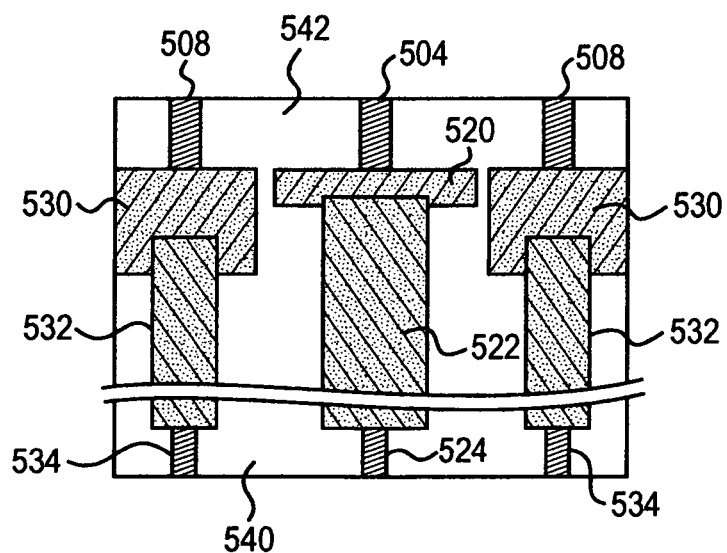
FIG. 14 is a cross-section of an exemplary three-dimensional device implementation taken along line 14-14 in FIG. 13.

FIG. 14 is a cross-section of an exemplary implementation taken along line 14-14 in FIG. 13. FIG. 14 thus shows features of the central zener diode and of two of the six triggering diodes in the circle around it.

Leads 520 and 522 are first and second leads, respectively, of the zener diode, and lead 522 is also an extended conductive channel that can be connected through conductive contact 524 to biasing voltage or to a return line (not shown) similar to features shown in FIGS. 7 and 10. Leads 530 and 532 are similarly first and second leads, respectively, of each triggering diode, and can respectively be connected through conductive contacts 508 and 534 to biasing voltages or to return lines (not shown); each lead 532 is also an extended conductive channel that can be connected to respective return lines. Each diode includes a respective p-n junction between its first and second leads.

The illustrated implementation could be fabricated in various ways, such as by ink jet printing of materials or with any other suitable 3D microfabrication techniques. Fabrication of the illustrated structure could be performed on a substrate (not shown), and the substrate could then be removed from the structure to obtain device 500. If device 500 is fabricated, e.g., with organic semiconductors, leads 520 and 530 could have one type of doping, while leads 522 and 532 could have the other, thus providing a p-n junction between the leads of each diode. Conductive contacts 504, 508, 524, and 534 could be conductive polymers, while surrounding insulating material 540 and 542 could be suitable insulating polymers.

Potential applications of techniques as described above include amplifying output from a network, such as from a neural network; selecting an output from a number of outputs, such as through interference between magnetic fields; synchronizing a collection of channels; and, more generally, transferring information from one set of channels to another for any appropriate purpose. An example of information transfer might also include a minimum or "cutoff" frequency, with current variations in the first set of channels only being transferred to the second set of channels if they are above a minimum frequency. In addition, the second set of channels could be prepared in an appropriate way prior to production of the respective electrical currents in the first set of channels. The respective electrical currents in the first set of channels could be synchronized or otherwise related in time.

Figure 15:
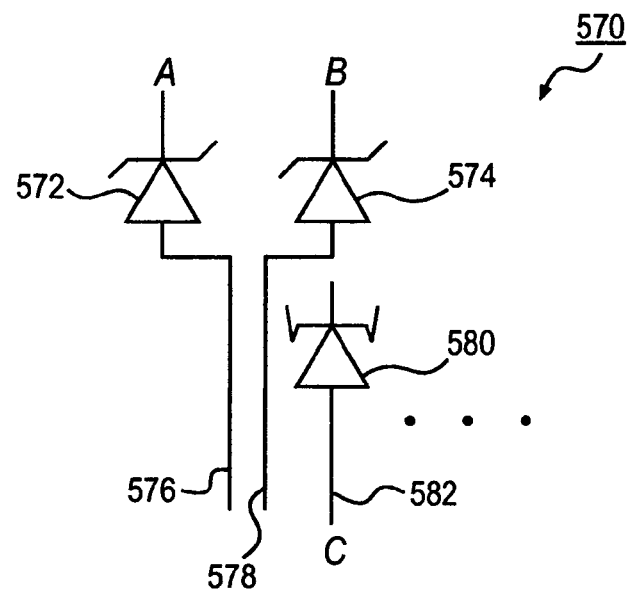
FIG. 15 is a schematic circuit diagram of a device with components similar to some of those in FIG. 9 and that can perform a logical operation.
Figure 16:
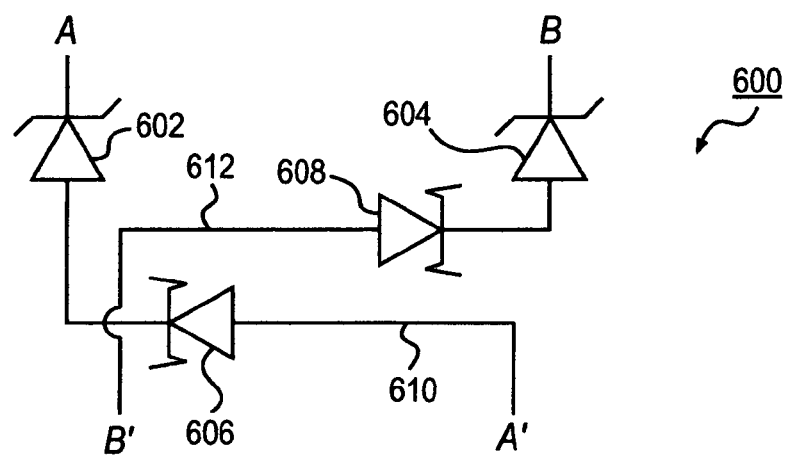
FIG. 16 is a schematic circuit diagram of a device with components similar to some of those in FIG. 9 and that can perform an operation similar to a logical operation.

Techniques illustrated in FIGS. 15 and 16 address the general problem of providing, for example, logical operations and timing operations using circuitry in which transient electrical circuits occur. Such operations would be useful if such circuitry were implemented for such purposes as data processing.

FIG. 15 shows device 570, which could be implemented with techniques as described above and which can be used to perform types of logical operations with two received operands, designated A and B, to obtain and provide a result C. Output of a transient electrical current above some threshold amplitude or range can represent one binary value, while output of a transient electrical current below the threshold (or absence of an output transient electrical current) can represent the other binary value.

In device 570, zener diodes 572 and 574 are illustratively connected to receive voltages representing binary values of operands A and B, respectively, possibly through a time-varying current source and a capacitive component as described above in relation to FIG. 7. When either of the received voltages reaches breakdown voltage for the respective diode, the diode provides a transient electrical current on the respective one of extended conductive channels 576 and 578. Channels 576 and 578 and EMF triggering component 580 are configured so that component 580 provides a transient electrical current if a criterion appropriate for a given logical operation is met. For example, for an OR operation, component 580 would provide a secondary transient electrical current if either or both of channels 576 and 578 carry a primary transient electrical current; for an AND operation, on the other hand, component 580 would provide a secondary transient electrical current only if both of channels 576 and 578 carry a primary transient electrical current.

In the illustrated implementation, extended conductive channel 582 is connected to receive a transient electrical current from component 580. As suggested by the ellipses at right in FIG. 15, a transient electrical current in extended conductive channel 582 could be amplified by cascading, such as with techniques as in FIG. 9.

FIG. 16 shows device 600, which could also be implemented with techniques as described above and which might be useful in performing some sorts of logic and timing operations with two received operands, designated A and B, to obtain and provide related results A' and B'. As in FIG. 15, output of a transient electrical current above some threshold amplitude or range can represent one binary value, while output of a transient electrical current below the threshold (or absence of an output transient electrical current) can represent the other binary value.

In device 600, zener diodes 602 and 604 are illustratively connected to receive voltages representing binary values of operands A and B, respectively, possibly through a time-varying current source and a capacitive component as described above in relation to FIG. 7. When either of the received voltages reaches breakdown voltage for the respective diode, the diode provides a transient electrical current to an input of a respective EMF triggering component 606 or 608.

In one variation, each of components 606 and 608 could be configured to be triggered by an EMF peak due to a transient electrical current from the other through the respective one of extended conductive channels 610 and 612. In this variation, after either of components 606 or 608 is first triggered, such as by an EMF peak from another extended conductive channel (not shown), the resulting transient electrical current in the respective one of channels 610 and 612 can then trigger the second of components 606 and 608, which can in turn trigger the first, and so forth. Therefore, if A and B are alternating values with appropriate timing, device 600 will similarly provide alternating values for A' and B'. In other situations, i.e. situations in which A and B are not alternating with appropriate timing, device 600 would not provide transient electrical currents in channels 610 and 612, i.e. for A' and B'.

In another variation, possibly more consistent with the arrangement shown in FIG. 16, each of components 606 and 608 is configured so that it is inhibited from being triggered by an EMF peak due to a transient electrical current from the other through the respective one of extended conductive channels 610 and 612, because, e.g., the direction of the EMF peak reduces or holds voltage across the component's p-n junction below breakdown rather than increasing voltage past breakdown. In this variation, after either of components 606 or 608 is first triggered, such as by an EMF peak from another extended conductive channel (not shown), the resulting transient electrical current in the respective one of channels 610 and 612 can then in effect turn off the second of components 606 and 608 temporarily, in a manner resembling repeated XOR operations.

The examples in FIGS. 15 and 16 are merely illustrative, and various other devices similar to those in FIGS. 15 and 16 could be implemented to perform these and other operations. Also, it may be possible to configure an EMF triggering component so that it is normally on and is instead turned off by a transient electrical current in a nearby extended conductive channel, providing a transient lack of electrical current at its output which might allow implementation of inversion or a NOT operation. Also, a number of devices as in FIGS. 15 and 16, together with other similar devices, could be combined to obtain circuitry to perform more complex logical operations. It may also be possible to combine such devices to perform timing functions such as pacemaking.

It now appears possible that microtubules or other cytoskeletal protein-based structures in dendrites of neurons can be triggered to provide transient electrical currents in a manner similar to EMF triggering components as described above, possibly leading to cascaded triggering and to series of amplified EM waveform peaks. Such phenomena might account for extracranial EM waveforms detected by electroencephalography (EEG) and magnetoencephalography (MEG) and might also play a role in changes of conscious experience, possibly including disorders of consciousness.

Devices implementing techniques as described above might also be implemented in brain implants or inserts that can cause or interact with EM waveforms in response to appropriate neural signals. The EM waveforms could be coupled, for example, to apical dendrites of pyramidal cells in human cerebral cortex.

Figure 17:
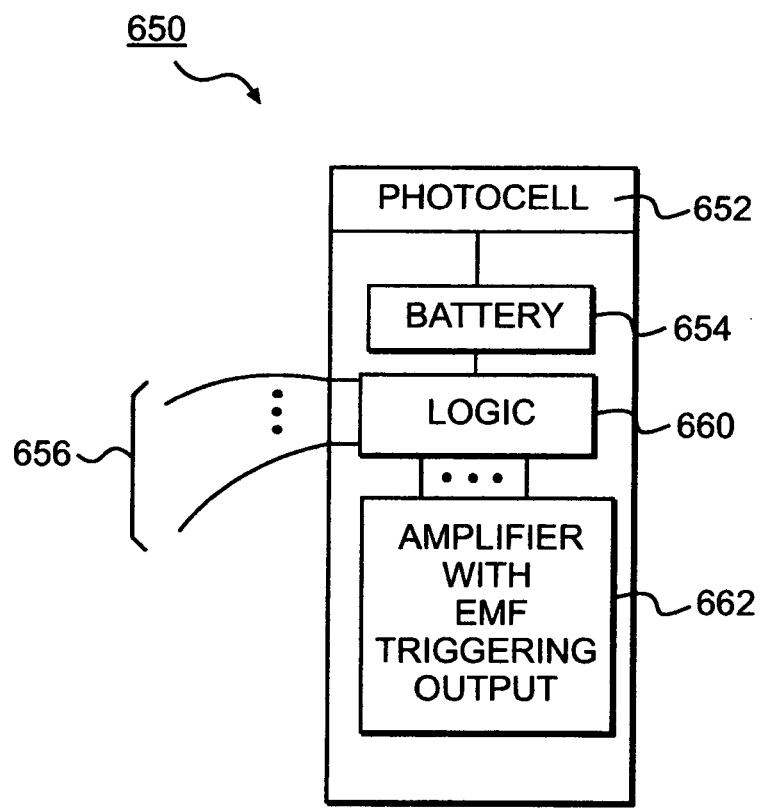
FIG. 17 is a schematic side view of an implantable device that includes an amplifier with EMF triggering output.

FIG. 17 illustrates an exemplary implementation intended to address the general problem of modifying or otherwise interacting with transient cytoskeletal electrical currents in brains. Various malfunctions or deficits might occur, such that a given region of a brain might not provide its appropriate contribution to EM waveforms. Implant 650 could be a tiny structure for insertion into a brain, produced by suitable small-scale manufacturing techniques such as micro- and nanofabrication; for example, the maximum outside dimension of implant 650 might be 5 mm, 1 mm, or less. Once inserted, implant 650 could operate as a sort of prosthetic device, for example, taking the place of a malfunctioning brain structure; or implant 650 could perform a corrective function, adjusting EM waveforms to compensate for problems in nearby brain structures.

Implant 650 illustratively includes photocell 652, a component that responds to photons by providing electrical current to charge battery 654; photons could be received, e.g. from a light source outside the brain, either through radiation into the brain or through a light conduit such as an optical fiber. Implant 650 also includes appropriate input devices that allow it to detect activity of nearby neurons, illustratively array 656 of input filaments or microelectrodes. Battery 654 provides power to logic 660, and logic 660 performs operations that control amplifier 662 in response to input from array 656. For example, in response to a particular combination of signals from array 656, logic 660 could control amplifier 662 to provide an appropriate amplified EM waveform.

Amplifier 662 could be implemented with circuitry as described above, including, e.g., an arrangement of EMF triggering components and extended conductive channels that can perform amplification by triggered cascading. In short, the output from amplifier 662 is produced by EMF triggering, and is therefore referred to as "EMF triggering output".

In addition to the specific exemplary implementations and applications described above, techniques as described herein could be implemented and applied in numerous other ways.

Some exemplary implementations include two sets of channels, one with EMF triggering components, but techniques as described herein could be implemented with more than two sets or with a different approach in which there are not separate sets of channels. Furthermore, in some exemplary implementations, current from a diode or other component is provided to a single extended conductive channel, but current from a single diode or other component could be provided to multiple extended conductive channels.

Some exemplary implementations include channels that do not move relative to each other, but techniques as described herein could be implemented with channels and EMF triggering components that move relative to each other and/or relative to surrounding magnetic flux patterns.

While the invention has been described in conjunction with specific exemplary implementations and applications, it is evident to those skilled in the art that many alternatives, modifications, and variations will be apparent in light of the foregoing description. Accordingly, the invention is intended to embrace all other such alternatives, modifications, and variations that fall within the spirit and scope of the claims now or hereafter appended.

The invention claimed is:

1. An article of manufacture comprising:
two or more channels, each channel having electrical conductivity that, in use, varies over time among a respective set of values that includes a substantially non-conductive value and at least one conductive value; the channels including at least one coupling group of channels, each coupling group being configured such that, in use, inductive coupling occurs between electrical currents in the coupling group of channels;
the channels further including first and second sets of the channels; the first set including one or more of the channels; the second set including one or more of the channels and including at least one channel that is not in the first set and that is in a coupling group with at least one channel in the first set; the channels in the first and second sets being configured so that, in response to electrical currents each in a respective one of the first set of the channels, a spatiotemporal magnetic flux pattern occurs that induces, in each of the second set of the channels, a respective electrical current variation that depends on the respective electrical currents in the first set of the channels and that increases magnetic flux density in at least part of the spatiotemporal magnetic flux pattern.

2. A method of using the article of claim 1, the method comprising:
in each of the first set of the channels, producing a respective electrical current; the act of producing a respective electrical current comprising:
producing the respective electrical currents of the channels in the first set so that the spatiotemporal magnetic flux pattern induces, in each of the second set of the channels, the respective electrical current variation.

3. The method of claim 2 in which the respective electrical current of each of the first set of the channels and the respective electrical current variation of each of the second set of channels are all transient electrical currents.

4. The method of claim 3 in which the act of producing a respective electrical current further comprises:
producing a transient electrical current in each of the first set of channels such that the transient electrical currents in the first and second set of channels produce an amplified electromagnetic (EM) waveform.

5. The method of claim 2 in which the method comprises a series of iterations, each iteration including an instance of the act of producing a respective electrical current.

6. The article of claim 1 in which the channels further include a third set of the channels that includes one or more of the channels and including at least one channel that is neither in the first set nor in the second set and that is in a coupling group with at least one channel in the second set; the channels in the second and third sets being configured so that, in response to electrical current variations induced in the second set of channels, a spatiotemporal magnetic flux pattern occurs that induces, in each of the third set of the channels, a respective electrical current variation that depends on the respective electrical current variations in the second set of the channels.

7. The article of claim 1 in which the channels are in one of:
a two-dimensional array; and
a three-dimensional arrangement.

8. The article of claim 1, further comprising:
a first current-providing component that includes a respective channel; one of the channels in the first set including the respective channel of the first current-providing component.

9. The article of claim 8 in which the first current-providing component includes at least one of:
a zener diode; and
a transistor.

10. The article of claim 8 in which the one channel in the first set further includes:
an extended conductive channel connected to receive electrical current from the first current-providing component's channel.

11. The article of claim 8, further comprising:
a return line connecting one channel in the first set to the first current-providing component to form a conductive loop.

12. The article of claim 1, further comprising:
a second current-providing component that includes a respective channel; one of the channels in the second set including the respective channel.

13. The article of claim 12 in which the second current-providing component includes at least one of:
   an EMF triggering component;
   a zener-like diode; and
   a transistor.

14. The article of claim 12 in which the one channel in the second set further includes:
   an extended conductive channel connected to receive electrical current from the second current-providing component's channel.

15. The article of claim 14, further comprising:
   a return line connecting the extended conductive channel to the second current-providing component to form a conductive loop.

16. The article of claim 1 in which one of:
   the channels in the first and second sets are all approximately parallel;
   at least one channel in the second set is not approximately parallel to a channel in the first set;
   at least one channel in the second set is connected in a conductive loop through which passes magnetic flux from electrical current in a channel in the first set;
   at least one channel in the second set includes a p-n junction that extends approximately perpendicular to a channel in the first set;
   the first set includes a first channel and the second set includes second and third channels adjacent to the first channel in a two-dimensional array; and
   the first set includes a first channel and the second set includes more than two channels adjacent to the first channel in a three-dimensional arrangement.

17. The article of claim 1 in which the article is an implant that can be inserted into a brain.

18. A system comprising:
   a channel component that includes two or more channels, each channel having electrical conductivity that, in use, varies over time among a respective set of values that includes a substantially non-conductive value and at least one conductive value; the channels including at least one coupling group of channels, each coupling group being configured such that, in use, inductive coupling occurs between electrical currents in the coupling group of channels;
   a processing component that includes one or more processors; and
   connecting circuitry that connects the processing component to the channel component;
   in operation, the processing component providing control signals through the connecting circuitry to the channel component that cause, in each of a first set of the channels, a respective electrical current; the first set including one or more of the channels; a spatiotemporal magnetic flux pattern occurring in response to the respective electrical currents of the first set of the channels; the processing component providing the control signals so that the spatiotemporal magnetic flux pattern induces, in each of a second set of the channels, a respective electrical current variation that depends on the respective electrical currents in the first set of the channels and that increases magnetic flux density in at least part of the spatiotemporal magnetic flux pattern; the second set including one or more of the channels and including at least one channel that is not in the first set and that is in a coupling group with at least one channel in the first set.

19. A method of using a configuration of electrical current channels; the configuration including:
   two or more channels, each channel having electrical conductivity that, in use, varies over time among a respective set of values that includes a substantially non-conductive value and at least one conductive value; the channels including at least one coupling group of channels, each coupling group being configured such that, in use, inductive coupling occurs between electrical currents in the coupling group of channels;
   the method comprising:
   producing a respective electrical current in each of a first set that includes one or more of the channels; the act of producing a respective electrical current comprising:
      producing the respective electrical currents of the channels in the first set so that a spatiotemporal magnetic flux pattern occurs; the spatiotemporal magnetic flux pattern inducing, in each of a second set of the channels, a respective electrical current variation; the second set including one or more of the channels and including at least one channel that is not in the first set and that is in a coupling group with at least one channel in the first set; in each of the second set of the channels, the respective electrical current variation depending on the respective electrical currents in the first set of the channels and the respective electrical current variation increasing magnetic flux density in at least part of the spatiotemporal magnetic flux pattern.

20. The method of claim 19 in which the respective electrical current of each of the first set of the channels and the respective electrical current variation of each of the second set of channels are all transient electrical currents.

* * * * *